US012571766B2

(12) United States Patent
Sohn et al.

(10) Patent No.: US 12,571,766 B2
(45) Date of Patent: Mar. 10, 2026

(54) METHOD FOR MEASURING YIELD STRENGTH OF 3D PRINTED METALLIC MEMBER USING MAGNETIC INCREMENTAL PERMEABILITY AND MEASUREMENT SYSTEM FOR THE SAME

(71) Applicant: Korea Advanced Institute of Science and Technology, Daejeon (KR)

(72) Inventors: Hoon Sohn, Daejeon (KR); Hyung Jin Lim, Daejeon (KR); Jongsu Lee, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 135 days.

(21) Appl. No.: 18/580,750

(22) PCT Filed: Jul. 19, 2022

(86) PCT No.: PCT/KR2022/010538
§ 371 (c)(1),
(2) Date: Jan. 19, 2024

(87) PCT Pub. No.: WO2023/003325
PCT Pub. Date: Jan. 26, 2023

(65) Prior Publication Data
US 2024/0328998 A1 Oct. 3, 2024

(30) Foreign Application Priority Data

Jul. 21, 2021 (KR) ........................ 10-2021-0095604

(51) Int. Cl.
| | |
|---|---|
| *G01N 27/72* | (2006.01) |
| *G01B 11/14* | (2006.01) |
| *G01N 33/204* | (2019.01) |

(52) U.S. Cl.
CPC ........... *G01N 27/72* (2013.01); *G01N 33/204* (2019.01); *G01B 11/14* (2013.01)

(58) Field of Classification Search
CPC ....... G01N 27/72; G01N 33/204; G01B 11/14
See application file for complete search history.

(56) References Cited

U.S. PATENT DOCUMENTS

| | | | | |
|---|---|---|---|---|
| 10,883,965 | B2 * | 1/2021 | Feng ...................... | G01N 27/82 |
| 2012/0306483 | A1 * | 12/2012 | Boenisch ............... | G01N 27/82 |
| | | | | 324/239 |
| 2019/0145931 | A1 * | 5/2019 | Feng ...................... | G01N 27/83 |
| | | | | 324/222 |

FOREIGN PATENT DOCUMENTS

| | | |
|---|---|---|
| JP | 2000-111588 A | 4/2000 |
| KR | 2010-0003808 A | 1/2010 |

(Continued)

OTHER PUBLICATIONS

CN102033107 (Year: 2011), Laser-electromagnetic ultrasonic method for nondestructive examination of thermal barrier coating and probe device.*

(Continued)

*Primary Examiner* — Reena Aurora
(74) *Attorney, Agent, or Firm* — DALY, CROWLEY, MOFFORD & DURKEE LLP

(57) ABSTRACT

For non-destructively measuring the yield strength of a metallic member using magnetic incremental permeability, a quasi-static excitation magnetic field is applied to two points of the metallic member, while a small alternating magnetic field generated by a transmitting coil is applied to the metal member. Intensity of the quasi-static excitation magnetic field applied to the metallic member is measured using a Hall sensor. The magnetic field induced by the magnetized metallic member is detected using a sensing coil. Using signals from the Hall sensor and the sensing coil, a revers- (Continued)

MAGNETIC FLUX
DENSITY (B)

MAGNETIC FLUX DENSITY
BY HIGH-FREQUENCY
MAGNETIC FIELD

MAGNETIC HYSTERESIS CURVE
OF MATERIAL BY
LOW-FREQUENCY (STATIC)
MAGNETIC FIELD

ΔB

MAGNETIC HYSTERESIS
CURVE BY HIGH FREQUENCY
MAGNETIC FIELD

HIGH-FREQUENCY
MAGNETIC FIELD

ΔH

MAGNETIC
FIELD (H)

ible permeability (MIP) of the metallic member is obtained. A grain size of the metallic member is obtained from the relationship between the reversible permeability and the grain size of the metallic member, and the yield strength of the metallic member is calculated using the grain size. The grain size and yield strength of the metallic member can be measured non-destructively.

20 Claims, 6 Drawing Sheets

(56) References Cited

FOREIGN PATENT DOCUMENTS

| KR | 2010-0108034 A | 10/2010 |
| KR | 10-1001616 B1 | 12/2010 |
| KR | 10-1094076 B1 | 12/2011 |
| KR | 2014-0019160 A | 2/2014 |
| KR | 10-2236149 B1 | 4/2021 |

OTHER PUBLICATIONS

Gupta et al., "Magnetic Incremental Permeability Non-Destructive Evaluation of 12 Cr—Mo—W—V Steel Creep Test Samples with Varied Ageing Levels and Thermal Treatments;" Journal Article from NDT and E International, No. 104; Available Online Apr. 1, 2019; 9 Pages.

Li et al., "A Fast and Non-Destructive Method to Evaluate Yield Strength of Cold-Rolled Steel Via Incremental Permeability;" Research Article from Journal of Magnetism and Magnetic Materials, No. 498; Available Online Nov. 4, 2019; 7 Pages.

International Search Report (with English Translation) dated Oct. 27, 2022 for International Application No. PCT/KR2022/010538; 5 Pages.

* cited by examiner

100

METHOD FOR MEASURING YIELD STRENGTH OF 3D PRINTED METALLIC MEMBER USING MAGNETIC INCREMENTAL PERMEABILITY AND MEASUREMENT SYSTEM FOR THE SAME

CROSS REFERENCE TO RELATED APPLICATIONS

This application is a U. S. National Stage Application of International application No. PCT/KR2022/010538 filed on Jul. 19, 2022 which is based upon and claims the benefit of priority to Korean Patent Application 10-2021-0095604, filed on Jul. 21, 2021 in the Korean Intellectual Property Office. The disclosures of the above-listed applications are hereby incorporated by reference herein in their entirety.

TECHNICAL FIELD

The present invention relates to a technical field of measuring the yield strength of metallic members, and more particularly to measuring the yield strength of the metallic members being printed during 3D printing.

BACKGROUND ART

The development of 3D printing technology has made it possible to efficiently produce metal parts with complex shapes. However, it has traditionally been possible to determine whether a 3D printed part has achieved desired mechanical properties only by performing a destructive tensile test on the part after it has been manufactured. If the post-production test shows that the 3D printed part failed to achieve the desired properties, the production effort was wasted. Even if defects occur at the beginning of production, the production cannot be stopped immediately, and extra costs are incurred for continuing the unnecessary production process. In addition, since the tensile test method requires destroying the printed part to analyze it, the burden of rising costs increases as the number of test objects increases.

On the other hand, a technology for real-time monitoring of damage to printed objects using laser technology and artificial neural network technology during 3D printing is known.

DISCLOSURE OF THE INVENTION

Problems to be Solved

An object of the present invention is to provide a method for measuring the yield strength of a metal member and a measurement system for measuring the yield strength of a metallic member that non-destructively estimates the grain size and yield strength of the metallic member using the magnetic incremental permeability (MIP) and the Hall Petch relationship.

Another object of the present invention is to provide a method for measuring the yield strength of a metal member and a measurement system for measuring the yield strength of a 3D printed metallic member under fabrication in real time in a non-contact and non-destructive manner using the MIP and Hall Petch relationship.

The problems to be solved by the present invention are not limited to those described above, but may be extended in various ways without departing from the spirit and scope of the present invention.

Means to Solve the Problems

A method for measuring a yield strength of a metallic member using magnetic incremental permeability (MIP), according to embodiments to realize the object of the present invention, includes applying a quasi-static excitation magnetic field generated by using an electromagnet to enter and exit through two points of a metallic member to be measured; applying an alternating magnetic field ($\Delta H$) smaller than the quasi-static excitation magnetic field generated by a transmitting coil to the metallic member to overlap with the quasi-static excitation magnetic field in parallel with the applying of the quasi-static excitation magnetic field; measuring an intensity of the quasi-static excitation magnetic field applied to interior of the metallic member using a Hall sensor; detecting, using a sensing coil, a magnetic field induced by the metallic member magnetized by the quasi-static excitation magnetic field and the alternating magnetic field ($\Delta H$); obtaining, using an output signal from the Hall sensor and a detection signal from the sensing coil, a reversible permeability (MIP) of the metallic member; obtaining a grain size of the metallic member from a relationship between the obtained reversible permeability (MIP) and the grain size of the metallic member; and calculating a yield strength of the metallic member using the obtained grain size.

In an exemplary embodiment, the yield strength $\sigma_y$ of the metallic member may be obtained by entering the obtained grain size of the metallic member into a Hall-Petch relationship equation, $$\sigma_y = \sigma_0 + \frac{K_y}{\sqrt{d}},$$

between the grain size, d, of the metallic member and the yield strength, $\sigma_y$, where $\sigma_0$ is a friction stress of the metallic member and $K_y$ is a constant.

In an exemplary embodiment, the metallic member may be a metallic member that is 3D-printed in real time using a metallic raw material.

In an exemplary embodiment, the relationship may be represented by a butterfly-shaped graph showing a variation of MIP according to the grain size of the metallic member.

In an exemplary embodiment, the method may further include adjusting a separation distance between a MIP measurement sensor, which comprises the electromagnet, the Hall sensor, the transmitting coil, and the sensing coil which are integrally combined, and the metallic member using a piezoelectric element that causes a thickness change or movement thereof depending on a magnitude of a driving voltage applied; measuring the separation distance between the MIP measurement sensor and the metallic member using a displacement measurement sensor; and calculating the separation distance between the MIP measurement sensor and the metallic member using a separation distance measurement signal output from the displacement measurement sensor.

In an exemplary embodiment, the separation distance measurement signal may be a signal of detecting laser light reflected from the metallic member by emitting laser light from the MIP measurement sensor to the metallic member.

Meanwhile, a system for measuring the yield strength of a metallic member using MIP according to embodiments to realize the object of the present invention includes an electromagnet, a Hall sensor, a transmitting coil, a sensing coil, and a central processing unit. The electromagnet includes a yoke comprising two legs and an electromagnet coil wound on the yoke, and is configured to magnetically excite a metallic member to be measured by allowing a flux of a quasi-static excitation magnetic field generated when a quasi-static current flows in the electromagnet coil to enter and exit through two spaced apart points of the metallic member. The Hall sensor is disposed between the two legs of the electromagnet and is configured to measure an intensity of the quasi-static excitation magnetic field applied to an interior of the metallic member. The transmitting coil is wound around the Hall sensor and is configured to generate an alternating magnetic field ($\Delta H$) smaller than the quasi-static excitation magnetic field while an alternating current flows and apply to the metallic member to overlap with the quasi-static excitation magnetic field. The sensing coil is wound around the Hall sensor and is configured to detect the quasi-static excitation magnetic field and a magnetic field induced by the metallic member magnetized by the alternating magnetic field ($\Delta H$). The central processing unit is configured to obtain the reversible permeability (MIP) of the metallic member using an output signal from the Hall sensor and the detection signal from the sensing coil, to obtain the grain size of the metallic member from a relationship between the obtained reversible permeability (MIP) and the grain size of the metallic member, and to calculate a yield strength of the metallic member using the obtained grain size. With this configuration, the system for measuring the yield strength of the metallic member is capable of non-destructively measuring the grain size and yield strength of the metallic member to be measured.

In an exemplary embodiment, the yield strength $\sigma_y$ of the metallic member may be obtained by entering the obtained grain size of the metallic member into a Hall-Petch relationship $$\sigma_y = \sigma_0 + \frac{K_y}{\sqrt{d}}$$

between the grain size d of the metallic member and the yield strength $\sigma_y$, where $\sigma_0$ is a friction stress of the metallic member and $K_y$ is a constant.

In an exemplary embodiment, the relationship may be represented by a butterfly-shaped graph showing a variation of MIP as a function of the grain size of the metallic member.

In an exemplary embodiment, the electromagnet may be a U-shaped or horseshoe-shaped electromagnet with two legs facing the two spaced apart points of the metallic member.

In an exemplary embodiment, end faces of the two legs may be tapered or sloped end faces that decrease in cross-sectional area toward the end faces, respectively.

In an exemplary embodiment, the system may further comprise a Hall sensor holder including a Hall sensor fixture configured to hold the Hall sensor and a coil winding portion around which the transmitting coil and the sensing coil are wound, thereby integrally coupling the aid Hall sensor, the transmitting coil and the sensing coil.

In an exemplary embodiment, the Hall sensor holder may include a cylindrical body formed axially with a Hall sensor mounting hole, in a center of bottom of the cylindrical body, into which the Hall sensor is inserted, and the coil winding portion may include a first winding groove and a second winding groove, formed circumferentially on a lower outer surface of the cylindrical body to enclose the Hall sensor mounting hole, around which the transmitting coil and the sensing coil are wound, respectively.

In an exemplary embodiment, the electromagnet may include an electromagnet coil; a U-shaped or horseshoe-shaped yoke, on which the electromagnet coil is wound, made of magnetic material and having first and second end faces. The electromagnet may be configured to provide a magnetic path such that a quasi-static excitation magnetic field generated when a current signal of a quasi-static excitation frequency flows through the electromagnet coil travels through the yoke and enters and exits through the first and second end faces, thereby allowing the quasi-static excitation magnetic field to pass through a predetermined section of the metallic member to be measured when the metallic member is in proximity to the first and second end faces.

In an exemplary embodiment, the system may further include a first measurement signal processing unit connected to the Hall sensor and configured to convert an output signal from the Hall sensor into first digital data to be provided to the central processing unit; a second measurement signal processing unit configured to convert an output voltage signal from the sensing coil into second digital data to be provided to the central processing unit; and a direct current power supply providing an operational voltage required for the Hall sensor.

In an exemplary embodiment, the system may further include a first waveform generator configured to generate a quasi-static low-frequency current signal; a signal amplifier configured to amplify the quasi-static low-frequency current signal generated by the first waveform generator to be provided to the electromagnet coil; a second waveform generator configured to generate a high-frequency alternating current signal to be provided to the transmitting coil; a first measurement signal processing unit connected to the Hall sensor to digitize an output signal from the Hall sensor; and a second measurement signal processing unit connected to the sensing coil to digitize a detection signal from the sensing coil.

In an exemplary embodiment, the system may further comprise a sensor displacement unit configured to adjust a separation distance between a MIP measurement sensor, in which the electromagnet, the Hall sensor, the transmitting coil, and the sensing coil are integrally combined, and the metallic member to be measured.

In an exemplary embodiment, the sensor displacement unit may include a piezoelectric element configured to adjust the separation distance between the MIP measurement sensor and the metallic member by causing a thickness change or movement of the piezoelectric element depending on a magnitude of a driving voltage applied; and a housing configured to support the piezoelectric element so that the thickness change or movement of the piezoelectric element is transmitted to the MIP measurement sensor. In this case, the central processing unit may be configured to generate and apply to the piezoelectric element the driving voltage necessary to control the thickness change or movement of the piezoelectric element.

In an exemplary embodiment, the system may further include a displacement measurement unit configured to measure the separation distance between the MIP measurement sensor and the metallic member to be measured. In this case, the central processing unit may be configured to control an operation of the displacement measurement unit and to calculate the separation distance between the MIP measurement sensor and the metallic member using an output signal from the displacement measurement unit.

In an exemplary embodiment, the displacement measurement unit may include a laser displacement measurement sensor configured to generate laser light, while fixed to the MIP measurement sensor, to be emitted to the metallic member, and detect a reflected laser light from the metallic member.

Effects of the Invention

According to exemplary embodiments of the present invention, the yield strength of a metallic member that is a magnetic material can be measured in a non-contact, non-destructive manner. Thus, losses due to destruction of finished products for testing physical properties such as yield strength can be avoided. In addition, the yield strength of metallic members can be measured in real time. It is possible to monitor in real time whether the yield strength of the metallic member being manufactured is properly secured. If it is determined that the metallic member being manufactured does not have the desired yield strength, it can be immediately discarded without proceeding to further fabrication or reinforced and remade, thereby minimizing losses due to defective products.

Exemplary embodiments of the present invention can be utilized in the process of 3D printing metallic members. The MIP sensor and the measurement system capable of MIP measurement can be mounted on a metal 3D printer to non-destructively measure the yield strength of a metal part being 3D printed in real time. Furthermore, the measurement results can be reflected in the 3D printing fabrication process to improve the durability of metal 3D printed products and structures and reduce the defect rate.

BEST MODE FOR CARRYING OUT THE INVENTION

Figure 1:
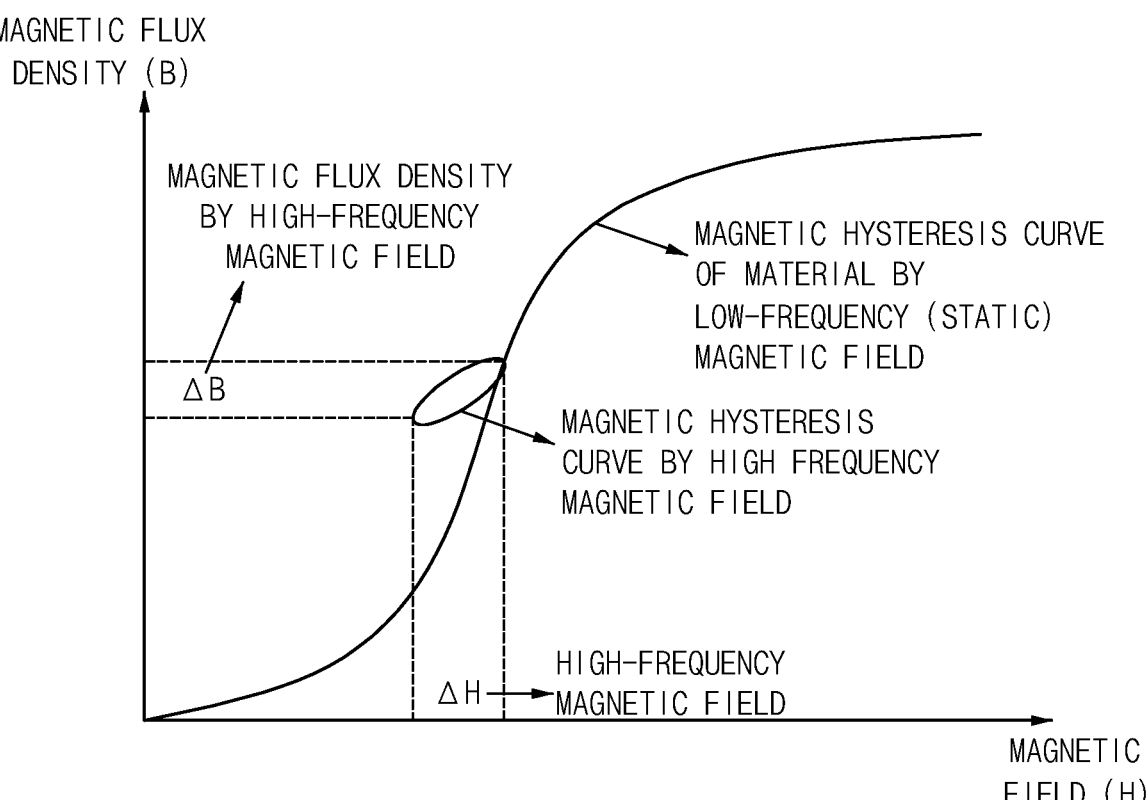
FIG. 1 is a diagram illustrating the relationship between MIP and grain size of a metallic member.

Hereinafter, preferred embodiments of the present invention will be described in more detail with reference to the accompanying drawings. The same reference numerals are used for identical components in the drawings, and duplicate descriptions of the same components are omitted.

FIG. 1 illustrates the relationship between MIP and grain size of a metallic member. Magnetic permeability is defined as the degree of response of a material to an applied magnetic field. Magnetic flux density (B) and magnetic field intensity (H) are correlated, but a shape of the B-H curve can vary greatly depending on the material. In magnetic materials, the magnetic flux density (B) does not change proportionally with the magnitude of the magnetic field intensity (H), but instead changes irreversibly, as shown in FIG. 1, resulting in a hysteresis loop. However, in a very small range of the hysteresis loop (between the two dashed lines in FIG. 1), B-H can be seen to have a reversible relationship, and the permeability in that range is called the reversible permeability, $\mu_A$. MIP is defined as the reversible permeability of a ferromagnetic material, such as a metal, measured by applying a small alternating magnetic field to the ferromagnetic material, which is exposed to a constant quasi-static magnetic field, to overlap with the quasi-static magnetic field. The expression for MIP, or reversible permeability, $\mu_A$, is as follows, $$\mu_A = \frac{1}{\mu_0} \frac{\Delta B}{\Delta H}, \tag{1}$$

where $\mu_0$ is the permeability in vacuum, $4\pi \times 10^{-7}$ H/m, and $\Delta H$ and $\Delta B$ represent the change in intensity of the alternating magnetic field applied to the ferromagnetic material and the change in magnetic flux density due to the alternating magnetic field, respectively.

MIP may be calculated by measuring the magnetic flux density of the minor loops in the magnetization process. Microstructural features of ferromagnetic materials, such as magnetic domains, can be easily affected by mechanical damage such as plastic deformation and fatigue damage. In general, MIP is influenced by the microstructure and grain size of the material. Therefore, MIP measurements can be used to non-destructively estimate the grain size of the metallic member to be measured. Specifically, if the grain size is large in a weak static magnetic field, the metallic member is easy to be magnetized by a high-frequency alternating magnetic field, but $\Delta B$ is large, so $\mu_A$ is also large. If the particle size is small, the magnetization is relatively poor. In addition, in a strong static magnetic field, $\mu_A$ is small when the grain size is large, but $\mu_A$ is large when the grain size is small. Using these relationships, the reversible permeability, u, or MIP, may be used to estimate the grain size.

Furthermore, it is known that there is a relationship between the grain size, d, and the yield strength, $\sigma_y$, of a metallic member, which is called the Hall Petch relationship, $$\sigma_y = \sigma_0 + \frac{K_y}{\sqrt{d}}, \tag{2}$$

where $\sigma_0$ represents the friction stress of the metallic member, and $K_y$ is a constant.

Therefore, if the grain size, d, of the metallic member is known, the yield strength, $\sigma_y$, of the metallic member can be estimated using the above Hall Petch relationship equation.

Eventually, the yield strength, $\sigma_y$, of the metallic member can be determined based on the reversible permeability, $\mu_A$, and the equation of Hall-Petch relationship. In other words, the reversible permeability, $\mu_A$, or MIP, can be obtained by measuring the change in magnetic flux density with the increment of magnetic field, and the grain size of the metallic member can be obtained based on the relationship between the change in MIP and the grain size of the metallic member, and then the yield strength, $\sigma_y$, of the metallic member can be obtained by substituting the obtained grain size into the Hall-Petch relationship equation (2). This method allows the yield strength, $\sigma_y$, of the metallic member to be estimated without destroying the metallic member.

To determine the yield strength of a metallic member being 3D printed, it is first necessary to measure the MIP. In an exemplary embodiment, an MIP measurement sensor and an MIP measurement system comprising the sensor may be provided to measure the MIP of a metallic member in real time in a non-contact, non-destructive manner.

Figure 2:
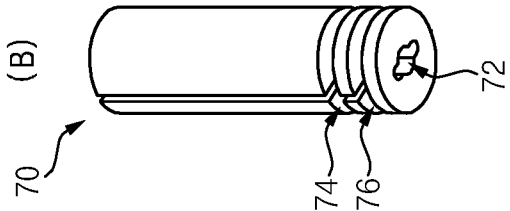
FIG. 2 illustrates a configuration of a MIP measurement sensor according to an exemplary embodiment of the present invention.
Figure 2:
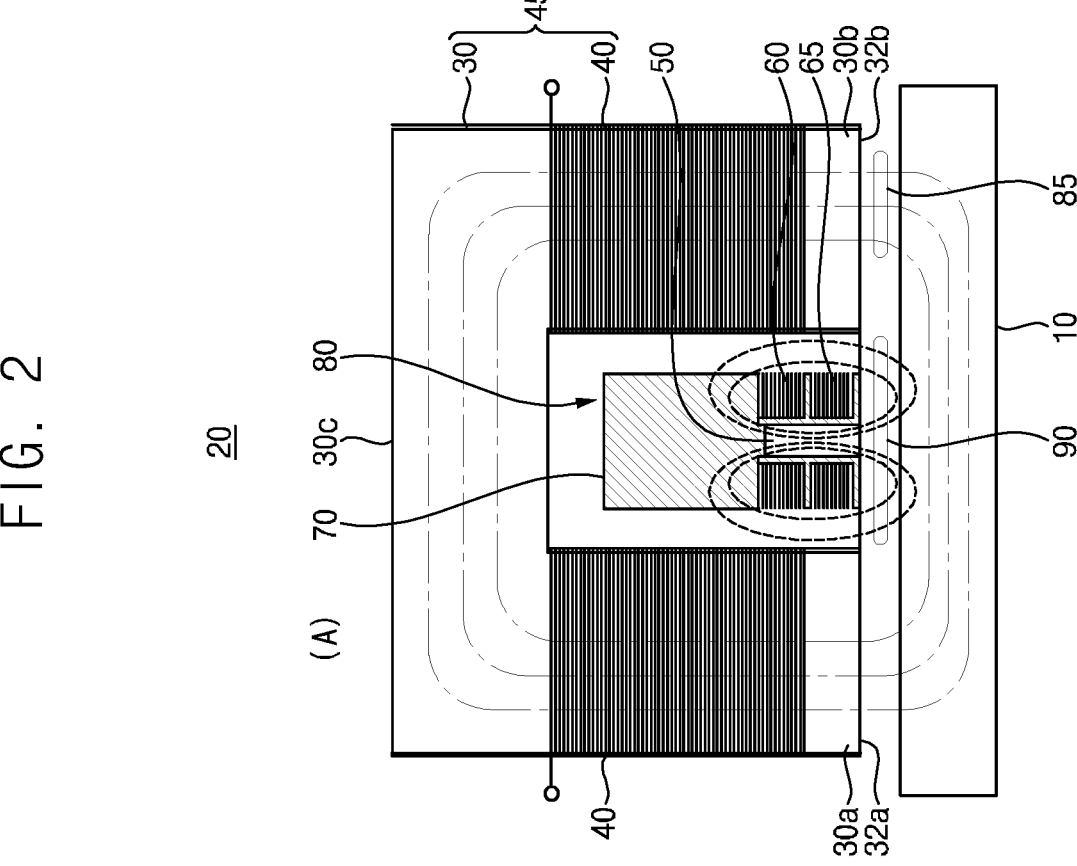

FIG. 2 illustrates a configuration of a MIP measurement sensor according to an exemplary embodiment.

Referring to FIG. 2, the MIP measurement sensor 20 may include an electromagnet 45 and a Hall sensor unit 80. The electromagnet 45 may include a yoke 30 and an electromagnet coil 40 wound around the yoke 30. The yoke 30 may function to provide a magnetic path that can focus the magnetic flux of the surrounding magnetic field and cause it to move through its interior. To accomplish this, the yoke 30 may be made of a magnetic material that enhances the focusing of the surrounding magnetic field. In an embodiment, the yoke 30 may be made of a ferromagnetic material, such as, for example, iron, nickel, or an alloy comprising each of these as a primary material.

The yoke 30 may have a structure including open sections, such as first and second leg portions 30a, 30b spaced apart by a predetermined distance and shaped as a horseshoe-shaped or U-shaped structure by a connection 30c connecting the tops of the two leg portions 30a, 30b. In one example, both end faces 32a, 32b of the two leg portions 30a, 30b may be substantially at the same level. In one example, both end faces 32a, 32b may be in a plane substantially parallel to a surface of the metallic member. For example, if the surface of the metallic member is planar, then the two end faces 32a, 32b may also be planes parallel to each other. The first and second legs 30a, 30b may be in the shape of a cylindrical column, or a polygonal column, such as a square column.

The electromagnet coil 40 may be wound on any section of the yoke 30. In one example, the first leg 30a and/or the second leg 30b of the yoke 30 may be wound with electromagnet coils 40 of high conductivity wire.

These electromagnets 45 may apply a quasi-static excitation magnetic field to the metallic member 10 to be measured. Let's consider a state in which the end faces 32a, 32b of the first and second legs 30a, 30b of the yoke 30 are proximate to the surface of the metallic member 10. A quasi-static excitation magnetic field 85 is generated around the electromagnet coil 40 by applying a sine wave current with a quasi-static excitation frequency to the electromagnet coil 40. The magnetic flux of the quasi-static excitation magnetic field 85 is concentrated within the yoke 30 and travels along the magnetic path provided by the yoke 30, as shown by the alternate long and short dash lines in FIG. 2. Then, the magnetic flux may exit the yoke 30 through any one of the end face 32a or 32b of the first and second legs 30a, 30b, entering the metallic member 10, magnetically exciting the metallic member 10 while traveling a predetermined distance, exiting the metallic member 10 again, entering the interior of the yoke 30 through the other end face 32a or 32b, and proceeding through the interior of the yoke 30 to the opposite end face 32a or 32b. In an exemplary embodiment, the quasi-static excitation magnetic field 85 may be a quasi-static magnetic field generated when a sinusoidal current with an excitation frequency of, for example, 0.1 Hz flows through the electromagnet coil 40. The intensity of the excitation magnetic field 85 may be about 10 kA/m.

In an exemplary embodiment, the Hall sensor unit 80 may be disposed between the first leg 30a and the second leg 30b of the yoke 30. The Hall sensor unit 80 may include a Hall sensor 50 and coil unit 60, 65.

The coil unit may include a transmitting coil 60 for applying a high-frequency alternating magnetic field 90 to the metallic member 10 to be measured, and a sensing coil 65 for measuring the magnetic field induced by the metallic member 10 to be measured.

As is well known, the Hall sensor is a sensor that can measure the intensity of a magnetic field. In the MIP measurement sensor 20, the Hall sensor 50 may be installed to measure the tangential intensity of a quasi-static excitation magnetic field 85 applied to the interior of the metallic member 10. In one example, the Hall sensor 50 may be disposed between the first leg 30a and the second leg 30b of the yoke 30. The Hall sensor 50 may be positioned substantially at the same level as the first end face 32a of the first leg 30a and the second end face 32b of the second leg 30b.

The transmitting coil 60 may be wound around the perimeter of the Hall sensor 50. The transmitting coil 60 can generate a small alternating magnetic field ΔH, during the flow of alternating current, which can be applied to the metallic member 10 to overlap with a large quasi-static excitation magnetic field (the definition of MIP). For this purpose, an alternating current of e.g. 50 kHz may be applied to the transmitting coil 60. The intensity of the alternating magnetic field ΔH may be small compared to the intensity of the quasi-static excitation magnetic field.

The sensing coil 65 may also be wound around the Hall sensor 50. A magnetic field may be generated around the metallic member 10 magnetized by the superposition of the large quasi-static excitation magnetic field applied by the electromagnet 45 and the small alternating magnetic field applied by the transmitting coil 60. The sensing coil 65 may detect an induced voltage induced by that magnetic field. The absolute value of the detected induced voltage may be proportional to the MIP, or reversible permeability, of the metallic member 10.

In an exemplary embodiment, to facilitate such an arrangement, the Hall sensor unit 80 may further include a Hall sensor holder 70 that integrally combines the Hall sensor 50, the transmitting coil 60, and the sensing coil 65. The Hall sensor holder 70 may include a Hall sensor fixture configured to hold the Hall sensor 50, and a coil winding portion around which the transmitting coil 60 and the sensing coil 65 may be wound. In an exemplary embodiment, as shown in (B) of FIG. 2, the Hall sensor holder 70 may be a cylindrical body, with an axially oriented Hall sensor mounting hole 72 at a bottom center of the cylindrical body as the Hall sensor fixture. Further, on the lower outer surface of the cylindrical body, a first winding groove 74 and a second winding groove 76 may be formed, one above and one below, to circumferentially surround the Hall sensor mounting hole 72 as coil winding parts of the transmitting coil 60 and the sensing coil 65, respectively.

Utilizing the Hall sensor holder 70, the Hall sensor 50 may be inserted into the Hall sensor mounting hole 72 and positioned substantially flush with the end faces 32a, 32b of the first and second legs 30a, 30b as noted above. The transmitting coil 60 and the sensing coil 65 may be wound in the first winding groove 74 and the second winding groove 76, respectively, so as to surround the Hall sensor 50, i.e., the sensing coil 65 may be wound so as to be located closer to the metallic member 10 to be measured than the transmitting coil 60. The transmitting coil 60 and the sensing coil are independent coils. The transmitting coil 60 is the coil that generates an alternating magnetic field corresponding to a high-frequency when a high-frequency alternating current flows, and the sensing coil 65 is a coil for measuring the magnetization of the metallic member 10 by detecting a third magnetic field induced from the metallic member 10. The alternating magnetic field generated by the transmitting coil 60 can be applied to the metallic member 10. The metallic member is magnetized by the quasi-static excitation magnetic field and the alternating magnetic field, and the magnetic field induced thereby induces a voltage in the sensing coil 65. The sensing coil 65 can detect and output the induced voltage.

Figure 3:
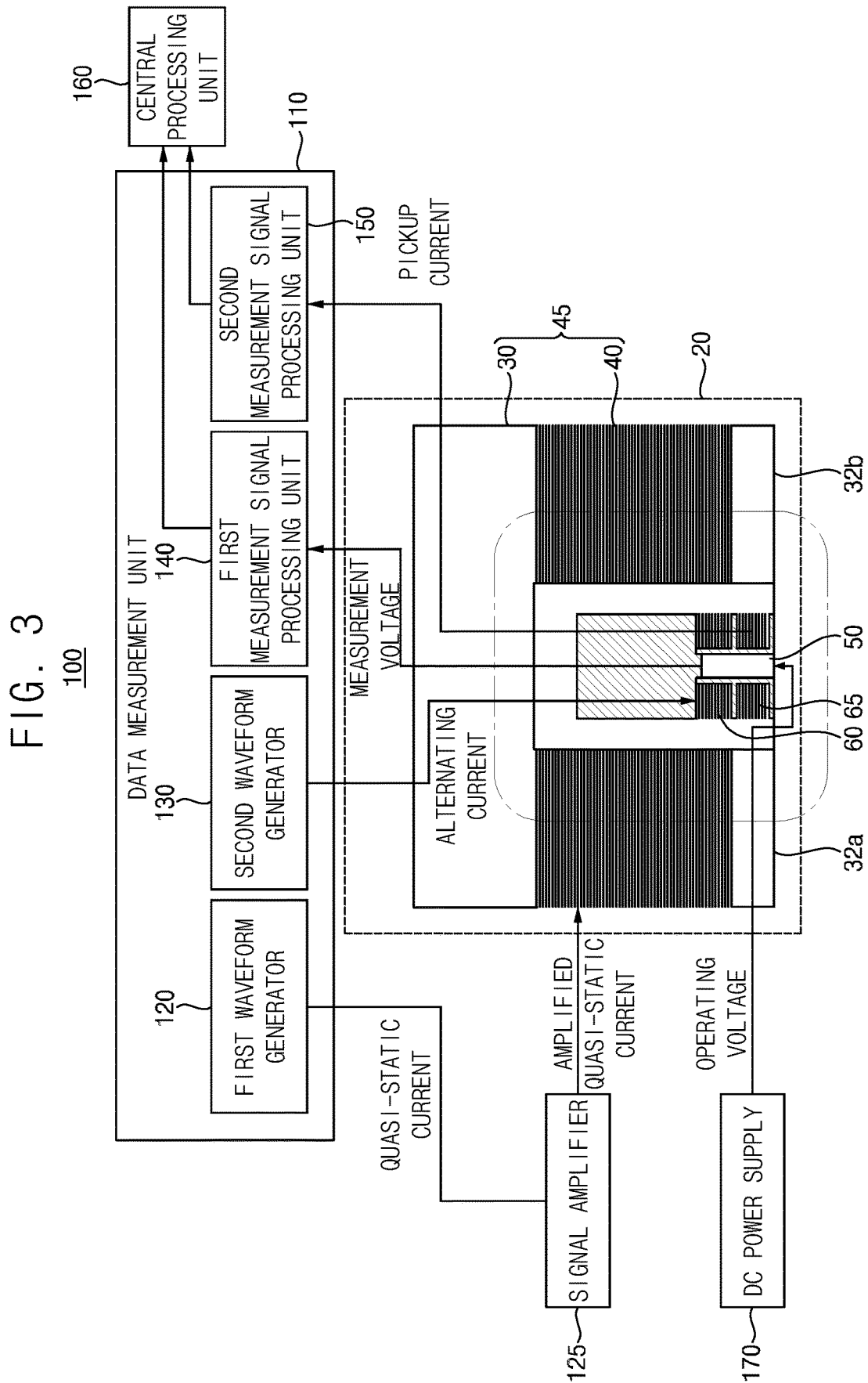
FIG. 3 illustrates a configuration of a MIP metrology system employing the MIP measurement sensor shown in FIG. 2.

FIG. 3 illustrates a configuration of a MIP measurement system employing the MIP measurement sensor shown in FIG. 2.

Referring to FIG. 3, the MIP measurement system 100 may further include, in addition to the MIP measurement sensor 20, a data measurement unit 110, a signal amplifier 125, a central processing unit 160, and a DC power supply 170.

The data measurement unit 110 may include first and second waveform generators 120, 130 and first and second measurement signal processing units 140, 150. The signal amplifier 125 may be connected between the first waveform generator 120 and the electromagnet coil 40 of the MIP sensor 20. The DC power supply 170 may be connected to a power terminal of the Hall sensor 50. The second waveform generator 130 may be connected to the transmitting coil 60. The first measurement signal processing unit 140 may be connected to an output terminal of the Hall sensor 50, and the second measurement signal processing unit 150 may be connected to the sensing coil 65.

The DC power supply 170 may provide the power required for the Hall sensor 50 to operate.

The first waveform generator 120 may generate a quasi-static low-frequency current signal. For example, the quasi-static low-frequency current signal may be amplified by the signal amplifier 125 into a current signal of sufficient large amplitude to be supplied to the electromagnet coil 40. As the amplified quasi-static low-frequency current flows through the electromagnet coil 40, a quasi-static low-frequency magnetic field may be generated to pass through the inside of the electromagnet coil 40. The magnetic flux of that quasi-static low-frequency magnetic field 85 may be concentrated within the yoke 30 and travel along the yoke 20 in the yoke 30 section, but in the non-yoke section between the two end faces 32a, 32b, pass through a medium present between the two end faces 32a, 32b. The medium may be air and the metallic member 10. In an exemplary embodiment, the first waveform generator 120 may generate a quasi-static sine wave, such as below 1 Hz. This causes the quasi-static low-frequency magnetic field 85 to also vary as a sine wave over time (hysteresis loop) (corresponding to step S10 in FIG. 6).

While the quasi-static low-frequency magnetic field 85 is applied to the metallic member 10, the second waveform generator 130 and the transmitting coil 60 may additionally apply a high-frequency alternating magnetic field 90 to the metallic member 10. That is, while the quasi-static low-frequency magnetic field 85 is applied to the metallic member 10, the second waveform generator 130 may generate and apply a high-frequency alternating current to the transmitting coil 60. In an exemplary embodiment, the second waveform generator 130 may generate a sinusoidal current of, for example, 1-10 kHz. As the high-frequency alternating current flows through the transmitting coil 60, a high-frequency alternating magnetic field 90 may be formed in the transmitting coil 60. The high-frequency alternating magnetic field 90 may be applied to the metallic member 10 to be measured while passing vertically through the Hall sensor 50 (corresponding to step S12 in FIG. 6).

The magnetization of the metallic member 10 by the quasi-static low-frequency magnetic field generated by the quasi-static current flowing in the electromagnet coil 40 may be measured using the Hall sensor 50 and the first measurement signal processing unit 140. The intensity of the quasi-static low-frequency magnetic field 85 applied to the metallic member 10 may be detected using the Hall sensor 50. The output signal from the Hall sensor 50 may be provided to the first measurement signal processing unit 140 and converted into a digital value, that is, the intensity of the quasi-static low-frequency magnetic field 85 applied to the metallic member 10 may be obtained as a digital value (corresponding to step S14 in FIG. 6).

Furthermore, when the high-frequency alternating magnetic field 90 generated by the transmitting coil 60 is applied to the metallic member 10, an eddy current may be generated in the metallic member 10, and the magnetic field induced thereby induces a voltage (or current) in the sensing coil 65. The induced current (induced voltage) flowing in the sensing coil 65 is provided to the second measurement signal processing unit 150 to be converted into a digital value (corresponding to step S14 in FIG. 6).

Even if while a quasi-static low-frequency magnetic field 85 is applied to the metallic member 10 to be measured, a high-frequency alternating magnetic field 90 of the same intensity is applied, the degree of magnetization of the metallic member 10 by the high-frequency alternating magnetic field 90 varies due to the reversible permeability of the metallic member 10 depending on the intensity of the quasi-static low-frequency magnetic field 85 being applied. This causes the magnitude of the eddy current signal measured by the sensing coil 65 and the second measurement signal processing unit 150 to vary.

Figure 4:
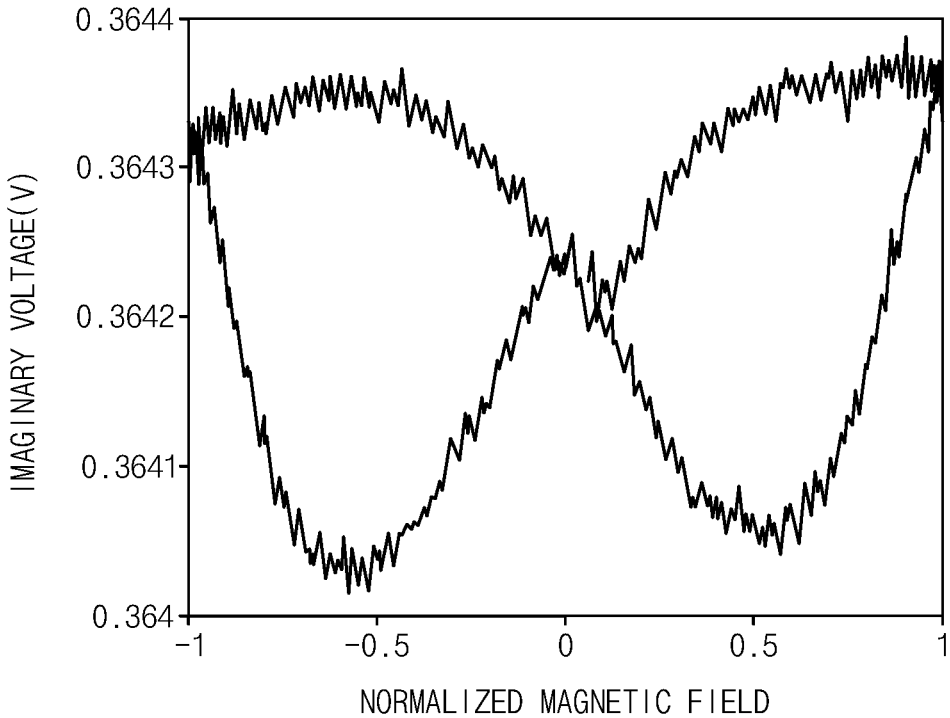
FIG. 4 illustrates a change in the magnetization of a metallic member to be measured by a quasi-static low-frequency magnetic field and a change in an eddy current signal due to further magnetization by a high-frequency alternating magnetic field.
Figure 6:
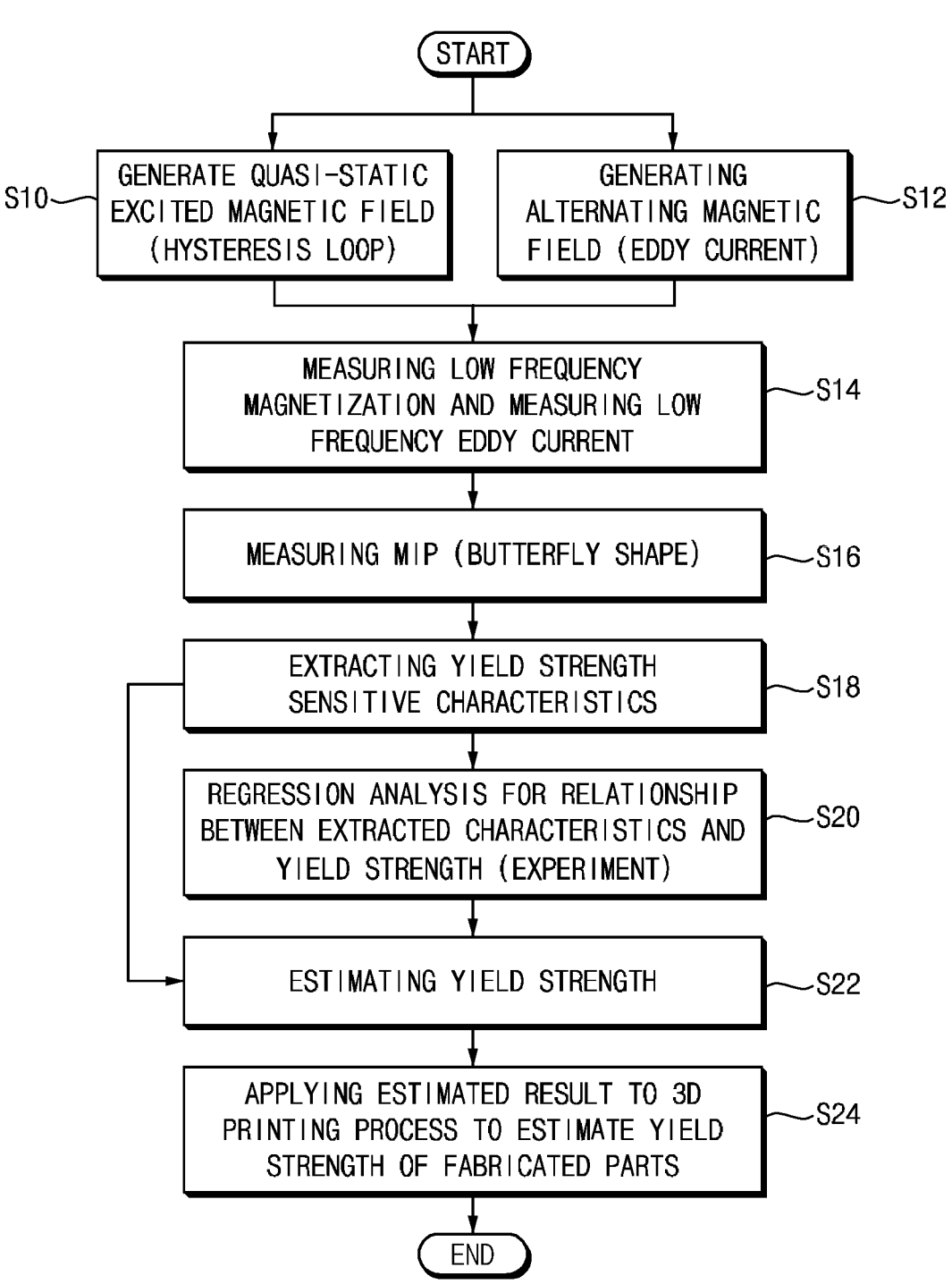
FIG. 6 is a flow chart of a method of measuring a metal 3D printing process based on the MIP method according to an exemplary embodiment of the present invention.

When the change in the magnetization of the metallic member 10 due to the quasi-static low-frequency magnetic field 85 measured by the first measurement signal processing unit 140 and the change in the eddy current signal due to further magnetization by the high-frequency alternating magnetic field 90 measured by the second measurement signal processing unit 150, may take the shape of a butterfly as shown in FIG. 4 (corresponding to step S16 in FIG. 6).

The MIP can be considered to be a measurement of the change in the degree of additional magnetization (reversible permeability) of the metallic member 10 under measurement by the high-frequency alternating magnetic field 90 according to the intensity of the quasi-static low-frequency magnetic field 85, which is known to be related to the grain size of the metallic member 10 under measurement. In a weak quasi-static low-frequency magnetic field, if the grain size of the metallic member 10 is large, the metallic member 10 is easy to be magnetized by the high-frequency alternating magnetic field, but if the grain size of the metallic member 10 is small, the magnetization of the metallic member 10 is relatively poor. Conversely, in a strong quasi-static low-frequency magnetic field, if the grain size of the metallic member 10 is large, the magnetization of the metallic member 10 by the high-frequency alternating magnetic field is not good, but if the grain size is small, the magnetization of the metallic member 10 is good.

Since the grain size is related to the yield strength of the material in the aforementioned Hall Petch relationship, the yield strength of the metallic member 10 to be measured can be estimated by measuring the MIP change according to the grain size, i.e., the butterfly shape shown in FIG. 4. In other words, since there is a relationship between 'change in butterfly shape→change in grain size of metallic member 10 to be measured→change in yield strength of metallic member 10 to be measured,' this relationship may be used to measure the grain size of metallic member 10 to be measured through MIP measurement of metallic member 10, and then to estimate the yield strength of metallic member 10 to be measured from the grain size (corresponding to step S18 in FIG. 6).

However, a quantitative relationship between the change in butterfly shape and the change in grain size is not yet known. Therefore, the yield strength may be estimated by simplifying the relationship to 'change in butterfly shape→change in yield strength'. For this purpose, a number of specimens of the same material but with different yield strengths may be manufactured. And, the characteristics related to the yield strength may be extracted from the butterfly shapes with respect to the specimens, and then the relationship between the extracted characteristics and the yield strength of the metallic member 10 to be measured can be found through regression analysis (corresponding to step S20 in FIG. 6).

Based on these points, the central processing unit 160 can obtain the reversible permeability (MIP) of the 3D printed metallic member 10 using the digital signal provided by the first measurement signal processing unit 140 (i.e., digital data of the output signal from the Hall sensor 50) and the digital signal provided by the second measurement signal processing unit 150 (i.e., digital data of the output voltage of the sensing coil 65). Then, the central processing unit 160 can obtain the grain size of the metallic member 10 from a relationship between the obtained reversible permeability (MIP) and the grain size of the metallic member 10, and calculate the yield strength of the metallic member 10 using the obtained grain size (corresponding to steps S22 and S24 in FIG. 6).

Figure 5:
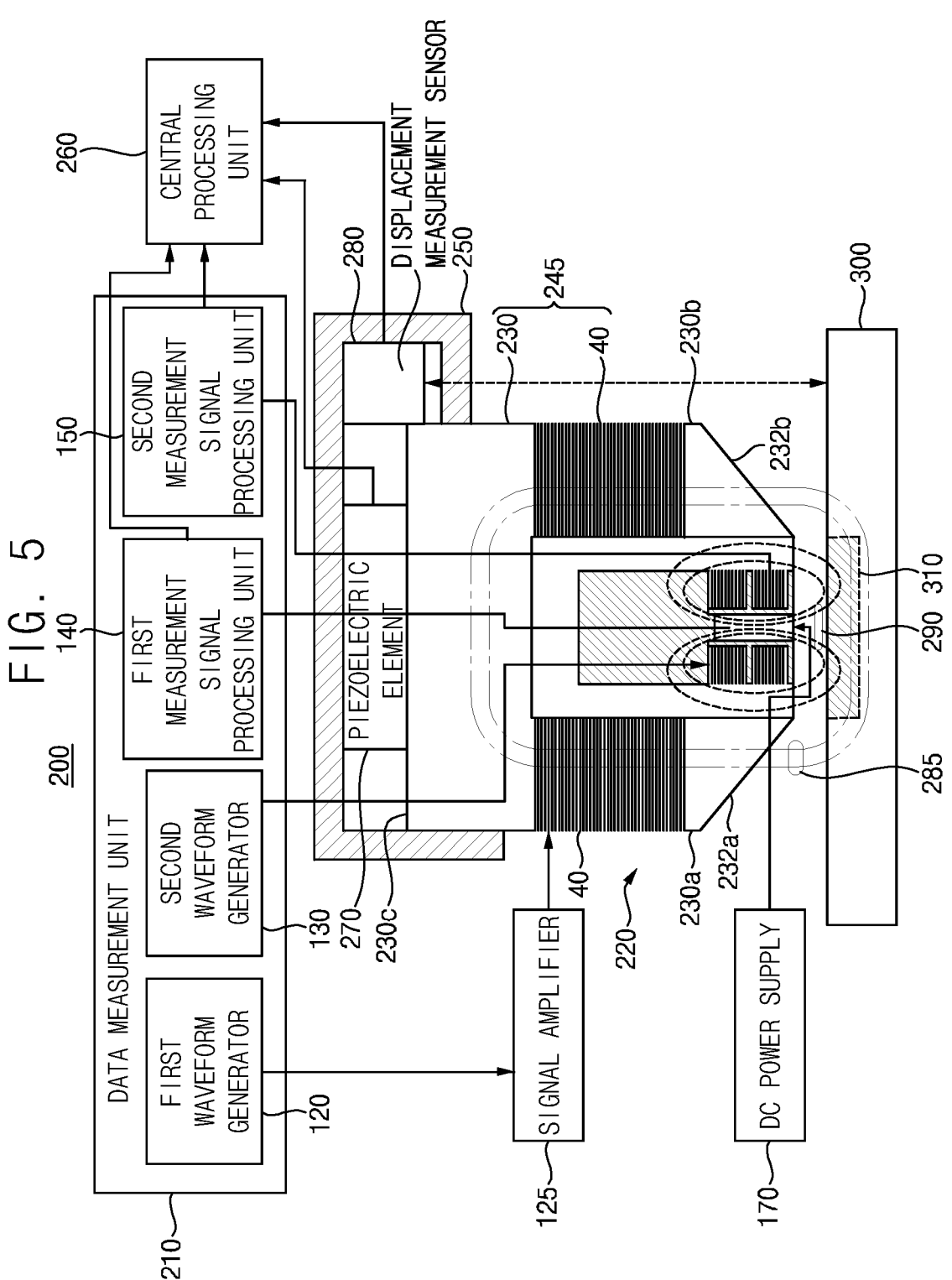
FIG. 5 illustrates a configuration of a system for measuring yield strength of 3D printed metallic member based on the MIP method, according to another exemplary embodiment of the present invention.

Next, FIG. 5 illustrates a configuration of a system for measuring yield strength of 3D printed metallic member based on the MIP method, according to another exemplary embodiment of the present invention.

When the yield strength of a 3D printed metallic member 300 is estimated using MIP, the separation (lift off) distance between the 3D printed metallic member 300 to be measured and a MIP measurement sensor 220 has a significant impact. Therefore, a means to precisely control and measure the lift off distance may be required. To this end, referring to FIG. 5, the system for measuring yield strength of 3D printed metallic member 200 may further include a sensor displacement unit, a displacement measurement unit, and a central processing unit 260 in addition to the components of the MIP measurement system 100 shown in FIG. 3.

The sensor displacement unit may be configured to adjust the lift off distance of the MIP measurement sensor 220 relative to the 3D printed metallic member 300 to be measured. For this purpose, in an exemplary embodiment, the sensor displacement unit may include a piezoelectric element 270 and a housing 250.

The piezoelectric element 270 is, as is known, an element capable of converting an electrical signal into mechanical strain when applied, such that applying a voltage to the piezoelectric element 270 can cause a thickness change or movement of the element.

The housing 250 may be configured to support the piezoelectric element 270 so that the thickness change or movement of the piezoelectric element 270 is transmitted to the MIP measurement sensor 220. The piezoelectric element 270 may be disposed in a form interposed between the MIP measurement sensor 220 and the housing 250 by the housing 250. For example, the piezoelectric element 270 may be disposed in a sandwiched configuration between the housing 250 and the connection 230c of the yoke 230 of the electromagnet 245.

Since the housing 250 is fixed in position, the yoke 230 can be displaced toward the 3D printed metallic member 300 by a change in the thickness of the piezoelectric element 270. By precisely controlling the electrical signal applied to the piezoelectric element 270, the thickness or movement of the piezoelectric element 270 can be adjusted, and the separation distance between the MIP measurement sensor 220 and the 3D printed metallic member 300 can be precisely adjusted to the micrometer level.

The displacement measurement unit may be configured to measure the separation distance between the 3D printed metallic member 300 and the MIP measurement sensor 220. In an exemplary embodiment, the displacement measurement unit may include a displacement measurement sensor 280. The displacement measurement sensor 280 may be a laser displacement measurement sensor configured to measure the separation distance between the 3D printed metallic member 300 and the MIP measurement sensor 220 using a laser. That is, the displacement measurement sensor 280 may generate and emit laser light to the 3D printed metallic member 300, and detect the laser light reflected from the 3D printed metallic member 300 and convert the received laser light into a corresponding electrical signal. The converted electrical signal may be utilized as a signal for calculating the separation distance between the 3D printed metallic member 300 and the MIP measurement sensor 220. For this purpose, the converted electrical signal may be converted to digital data and provided to the central processing unit 260.

In addition to calculating the grain size and yield strength of the metallic member 300 by processing the data provided by the first and second measurement signal processing units 140, 150 described above, the central processing unit 260 may be configured to generate and apply to the piezoelectric element 270 a driving voltage necessary to adjust a thickness change or movement of the piezoelectric element 270. In addition, the central processing unit 260 may control the operation of the displacement measurement sensor 280 and receive an output signal from the displacement measurement sensor 280 to calculate the separation distance between the 3D printed metallic member 300 and the MIP measurement sensor 220.

In an exemplary embodiment, the first and second legs 230a, 230b of the yoke 230 of the electromagnet 245 may have a tapered shape with a decreasing cross-sectional area from a predetermined height of the first and second legs 230a, 230b to their respective lower ends. In another example, the end faces 232a, 232b of the first and second legs 230a, 230b may each have a sloped shape, for example, as illustrated in FIG. 5. When the end faces 232a, 232b of the first and second legs 230a, 230b of the yoke 230 are arranged in such a shape, the magnetic field induced by the electromagnet coil 40 can be collected at the end faces 232a, 232b, and it is possible to apply the magnetic field to only a small area, thereby obtaining a spatial resolution of the yield strength measurement in millimeters.

Thus, the system for measuring yield strength of 3D printed metallic member 200 according to an embodiment of the present invention may be mounted on a metal 3D printer to measure the yield strength of a metallic member under fabrication. The measurement results may be incorporated into the fabrication process to improve the safety and durability of 3D printed metallic products and structures and reduce the failure rate.

FIG. 6 illustrates a flowchart of a method of measuring a metal 3D printing process based on the MIP method, according to an exemplary embodiment of the present invention.

Referring to FIG. 6, a quasi-static low-frequency current signal may be generated by the first waveform generator 120 to be applied to the electromagnet coil 40 via the signal amplifier 125, thereby generating a quasi-static low-frequency magnetic field 285 that penetrates the electromagnet coil 40 and circumnavigates the yoke 230 (step S10). With the MIP measurement sensor 220 in close proximity to the 3D printed metallic member 300 to be metered, the quasi-static low-frequency magnetic field 285 generated by the electromagnet coil 40 may exit one of the two pointed end faces 232a, 232b of the yoke 230, penetrate a portion of the 3D printed metallic member 300 to be measured, i.e., the physical property metrology region 310, and then re-enter the other end face.

At the same time, a high-frequency alternating current applied to the transmitting coil 60 by the second waveform generator 130 may generate a high-frequency alternating magnetic field that passes through the transmitting coil 60 and the Hall sensor 50 (step S12). This high-frequency alternating magnetic field 290 may also pass through the property measurement area 310.

At this time, the Hall sensor 50 can detect a tangential component of the magnetic field caused by both of the quasi-static low-frequency magnetic field 310 and the high-frequency alternating magnetic field 290 which are overlapped with each other in the property measurement area 310, and provide the detected signal of tangential component to the first measurement signal processing unit 140. The first measurement signal processing unit 140 may amplify the detected signal, and convert the amplified signal to a digital signal to be provided to the central processing unit 260. At the same time, the sensing coil 65 may also detect a voltage induced by a magnetic field generated by a high-frequency eddy current in the property measurement area 310 and provide the detected voltage signal to the second measurement signal processing unit 150. The second measurement signal processing unit 150 may also amplify the received voltage signal, and convert the amplified signal to a digital signal to be provided to the central processing unit 260 (step S14).

Using the digital signals provided by the first and second measurement signal processing units 140, 150, the central processing unit 260 can calculate the grain size of the 3D printed metallic member 300 and a corresponding yield strength (steps S16-S24). More specifically, 3D printing can fabricate a member by stacking materials. When stacking a single layer thickness (about 100-200 μm) of a metallic material by 3D-printing, a portion of the existing stack at the bottom may melt, which may cause a change in the grain size of the 3D printed metallic material 300 and a corresponding change in the yield strength. In view of this, a method of adjusting the frequency and intensity of the input signal of the MIP measurement sensor 220 may be used to control the depth to which the eddy current can affect (e.g., 100 to 300 μm) and perform yield strength measurements to a target depth. It is known that the effective depth affected by the high-frequency eddy current has the following relationship (steps S16, and S18), $$\delta = \frac{1}{\sqrt{f\pi\mu\sigma}}, \tag{3}$$

where f is the frequency of the high-frequency eddy current input signal, μ is the permeability of the 3D printed metallic member 300, and σ is the electrical conductivity of the 3D printed metallic member 300. By adjusting the frequency of the high-frequency eddy current input signal using this equation, the eddy current effective depth can be controlled in the 3D printed metallic member 300 with known permeability and electrical conductivity. During metal 3D printing, the yield strength of each stacked layer of the metallic member 300 being fabricated can be estimated in a real-time, non-contact, and non-destructive manner, and the yield strength of the member can be estimated by combining the layer-by-layer estimation results with the G-code geometry information. Here, the G-code geometry information can be a design drawing for 3D printing that contains information about the geometry of the member to be produced and the lamination method. By adding the measured yield strength information for each layer to the G-code geometry information, the yield strength of the entire 3D printed metallic member 300 can be estimated through analysis (steps S20 to S24).

The central processing units 160, 260 of FIGS. 3 and 5 may be implemented as hardware components, software components, and/or a combination of hardware components and software components. For example, in embodiments, the central processing units 160, 260 may be implemented using one or more general purpose or special purpose computers, such as a processor, controller, arithmetic logic unit (ALU), digital signal processor, microcomputer, field programmable array (FPA), programmable logic unit (PLU), microprocessor, or any other device capable of executing and responding to instructions. The processing unit of the central processing unit 160, 260 may perform an operating system (OS) and one or more software applications run on the operating system. The processing devices of the central processing units 160, 260 may also access, store, manipulate, process, and generate data in response to execution of the software. For ease of understanding, the processing device is sometimes described as utilizing a single processing element, but one of ordinary skill in the art will recognize that the processing device may include a plurality of processing elements and/or a plurality of types of processing elements. For example, the processing device may include a plurality of processors or one processor and one controller.

The software of the central processing units 160, 260 may include computer programs, code, instructions, or one or more combinations thereof, and may configure the processing units to operate as desired, or may independently or collectively instruct the processing units. The software of the central processing units 160, 260 may be implemented in the form of program instructions that can be executed through various computer means and recorded on a computer-readable medium. The computer-readable medium may include program instructions, data files, data structures, and the like, singly or in combination. The program instructions recorded on the medium may be specifically designed and configured for the embodiment or may be known and available to those skilled in the art of computer software. Examples of computer-readable recording media include magnetic media such as hard disks, floppy disks, and magnetic tapes; optical media such as CD-ROMs and DVDs; magneto-optical media such as floptical disks; and hardware devices specifically configured to store and perform program instructions such as ROMs, RAMs, flash memory, and the like. Examples of program instructions include machine language code, such as that created by a compiler, as well as high-level language code that can be executed by a computer using an interpreter or the like. The aforementioned hardware devices may be configured to operate as one or more software modules to perform the operations of the embodiments, and vice versa.

INDUSTRIAL APPLICABILITY

The present invention can be used, for example, for measuring the yield strength of ferromagnetic materials, such as metals, and is particularly applicable to 3D printing with metallic members, where it can be useful for non-destructive, real-time monitoring of the yield strength of metallic members being 3D-printed.

Although the above embodiments have been illustrated by way of limited drawings, it will be understood by those skilled in the art that various modifications and changes can be made to the present invention without departing from the ideas and scope of the present invention as set forth in the following patent claims. Therefore, other implementations, other embodiments, and things that are equivalent to the claims of the patent are also within the scope of the following claims.

What is claimed is:

1. A method of measuring a yield strength of a metallic member using magnetic incremental permeability (MIP), including:

applying a quasi-static excitation magnetic field generated by using an electromagnet to enter and exit through two points of a metallic member to be measured;

applying an alternating magnetic field smaller than the quasi-static excitation magnetic field generated by a transmitting coil to the metallic member to overlap with the quasi-static excitation magnetic field in parallel with the applying of the quasi-static excitation magnetic field;

measuring an intensity of the quasi-static excitation magnetic field applied to interior of the metallic member using a Hall sensor;

detecting, using a sensing coil, a magnetic field induced by the metallic member magnetized by the quasi-static excitation magnetic field and the alternating magnetic field;

obtaining, using an output signal from the Hall sensor and a detection signal from the sensing coil, a reversible permeability of the metallic member;

obtaining a grain size of the metallic member by calculating the grain size based on a relationship between the obtained reversible permeability and the grain size of the metallic member; and calculating a yield strength of the metallic member using the obtained grain size.

2. The method of claim 1, wherein the yield strength, $\sigma_y$, of the metallic member is obtained by entering the obtained grain size of the metallic member into a Hall-Petch relationship equation, $$\sigma_y = \sigma_0 + \frac{K_y}{\sqrt{d}},$$

between the grain size, d, of the metallic member and the yield strength, $\sigma_y$, where $\sigma_0$ is a friction stress of the metallic member and $K_y$ is a constant.

3. The method of claim 1, wherein the metallic member is a metallic member that is 3D-printed in real time using a metallic raw material.

4. The method of claim 1, wherein the relationship is represented by a butterfly-shaped graph showing a variation of MIP according to the grain size of the metallic member.

5. The method of claim 1, further including adjusting a separation distance between a MIP measurement sensor, which comprises the electromagnet, the Hall sensor, the transmitting coil, and the sensing coil which are integrally combined, and the metallic member using a piezoelectric element that causes a thickness change or movement thereof depending on a magnitude of an driving voltage applied; measuring the separation distance between the MIP measurement sensor and the metallic member using a displacement measurement sensor; and calculating the separation distance between the MIP measurement sensor and the metallic member using a separation distance measurement signal output from the displacement measurement sensor.

6. The method of claim 5, wherein the separation distance measurement signal is a signal obtained by detecting laser light reflected from the metallic member when emitting laser light from the MIP measurement sensor to the metallic member.

7. A system for measuring a yield strength of a metallic member using magnetic incremental permeability (MIP), comprising:

an electromagnet including a yoke comprising two legs and an electromagnet coil wound on the yoke, and configured to magnetically excite a metallic member to be measured by allowing a flux of a quasi-static excitation magnetic field generated when a quasi-static current flows in the electromagnet coil to enter and exit through two spaced apart points of the metallic member;

a Hall sensor disposed between the two legs of the electromagnet and configured to measure an intensity of the quasi-static excitation magnetic field applied to an interior of the metallic member;

a transmitting coil wound around the Hall sensor and configured to generate an alternating magnetic field smaller than the quasi-static excitation magnetic field while an alternating current flows and apply to the metallic member to overlap with the quasi-static excitation magnetic field;

a sensing coil wound around the Hall sensor and configured to detect the quasi-static excitation magnetic field and a magnetic field induced by the metallic member magnetized by the alternating magnetic field; and a central processing unit configured to obtain a reversible permeability of the metallic member using an output signal from the Hall sensor and a detection signal from the sensing coil, to obtain a grain size of the metallic member by calculating the grain size based on a relationship between the obtained reversible permeability and the grain size of the metallic member, and to calculate a yield strength of the metallic member using the obtained grain size, wherein the system is capable of non-destructively measuring the grain size and yield strength of the metallic member to be measured.

8. The system of claim 7, wherein the yield strength $\sigma_y$ of the metallic member is obtained by entering the obtained grain size of the metallic member into a Hall-Petch relationship equation, $$\sigma_y = \sigma_0 + \frac{K_y}{\sqrt{d}},$$

between the grain size, d, of the metallic member and the yield strength, $\sigma_y$, where $\sigma_0$ is a friction stress of the metallic member and $K_y$ is a constant.

9. The system of claim 7, wherein the relationship is represented by a butterfly-shaped graph showing a variation of MIP according to the grain size of the metallic member.

10. The system of claim 7, wherein the electromagnet is a U-shaped or horseshoe-shaped electromagnet with two legs facing the two spaced apart points of the metallic member.

11. The system of claim 7, wherein end faces of the two legs are tapered or sloped end faces that decrease in cross-sectional area toward the end faces, respectively.

12. The system of claim 7, further comprising a Hall sensor holder including a Hall sensor fixture configured to hold the Hall sensor and a coil winding portion around which the transmitting coil and the sensing coil are wound, thereby integrally coupling the Hall sensor, the transmitting coil and the sensing coil.

13. The system of claim 12, wherein the Hall sensor holder includes a cylindrical body formed axially with a Hall sensor mounting hole, in a center of bottom of the cylindrical body, into which the Hall sensor is inserted, and wherein the coil winding portion includes a first winding groove and a second winding groove, formed circumferentially on a lower outer surface of the cylindrical body to enclose the Hall sensor mounting hole, around which the transmitting coil and the sensing coil are wound, respectively.

14. The system of claim 7, wherein the electromagnet includes an electromagnet coil; a U-shaped or horseshoe-shaped yoke, around which the electromagnet coil is wound, made of magnetic material and having first and second end faces, wherein the electromagnet is configured to provide a magnetic path such that a quasi-static excitation magnetic field generated when a current signal of a quasi-static excitation frequency flows through the electromagnet coil travels through the yoke and enters and exits through the first and second end faces, thereby allowing the quasi-static excitation magnetic field to pass through a predetermined section of the metallic member to be measured when the metallic member is in proximity to the first and second end faces.

15. The system of claim 7, further comprising a first measurement signal processing unit connected to the Hall sensor and configured to convert an output signal from the Hall sensor into first digital data to be provided to the central processing unit; a second measurement signal processing unit configured to convert an output voltage signal from the sensing coil into second digital data to be provided to the central processing unit; and a direct current power supply providing an operational voltage required for the Hall sensor.

16. The system of claim 7, further comprising a first waveform generator configured to generate a quasi-static low-frequency current signal; a signal amplifier configured to amplify the quasi-static low-frequency current signal generated by the first waveform generator to be provided to the electromagnet coil; a second waveform generator configured to generate a high-frequency alternating current signal to be provided to the transmitting coil; a first measurement signal processing unit connected to the Hall sensor to digitize an output signal from the Hall sensor; and a second measurement signal processing unit connected to the sensing coil to digitize a detection signal from the sensing coil.

17. The system of claim 7, further comprising a sensor displacement unit configured to adjust a separation distance between a MIP measurement sensor, in which the electromagnet, the Hall sensor, the transmitting coil, and the sensing coil are integrally combined, and the metallic member to be measured.

18. The system of claim 17, wherein the sensor displacement unit includes a piezoelectric element configured to adjust the separation distance between the MIP measurement sensor and the metallic member by causing a thickness change or movement of the piezoelectric element depending on a magnitude of a driving voltage applied; and a housing configured to support the piezoelectric element so that the thickness change or movement of the piezoelectric element is transmitted to the MIP measurement sensor, wherein the central processing unit is configured to generate and apply to the piezoelectric element the driving voltage necessary to control the thickness change or movement of the piezoelectric element.

19. The system of claim 17, further comprising a displacement measurement unit configured to measure the separation distance between the MIP measurement sensor and the metallic member to be measured, and wherein the central processing unit is configured to control an operation of the displacement measurement unit and to calculate the separation distance between the MIP measurement sensor and the metallic member using an output signal from the displacement measurement unit.

20. The system of claim 19, wherein the displacement measurement unit includes a laser displacement measurement sensor configured to generate laser light, while fixed to the MIP measurement sensor, to be emitted to the metallic member, and detect a reflected laser light from the metallic member.

\* \* \* \* \*